United States Patent
Graumann et al.

(10) Patent No.: US 6,317,621 B1
(45) Date of Patent: Nov. 13, 2001

(54) METHOD AND DEVICE FOR CATHETER NAVIGATION IN THREE-DIMENSIONAL VASCULAR TREE EXPOSURES

(75) Inventors: Rainer Graumann, Hoechstadt; Norbert Rahn, Erlangen, both of (DE)

(73) Assignee: Siemens Aktiengesellschaft, Munich (DE)

(*) Notice: Subject to any disclaimer, the term of this patent is extended or adjusted under 35 U.S.C. 154(b) by 0 days.

(21) Appl. No.: 09/559,044

(22) Filed: Apr. 27, 2000

(30) Foreign Application Priority Data

Apr. 30, 1999 (DE) .............................. 199 19 907

(51) Int. Cl.⁷ .................................................. A61B 5/00
(52) U.S. Cl. ...................... 600/424; 600/426; 600/427; 378/62
(58) Field of Search ..................... 600/424, 130, 600/425, 429, 443, 439, 407; 378/206, 198, 197, 205, 62

(56) References Cited

U.S. PATENT DOCUMENTS 5,274,551 * 12/1993 Corby ............................ 364/413.13
5,588,033 * 12/1996 Yeung ...................................... 378/4
5,851,183    12/1998 Bucholz .
5,871,445     2/1999 Bucholz .

* cited by examiner

*Primary Examiner*—Marvin M. Lateef
*Assistant Examiner*—Eleni Mantis Mercader
(74) *Attorney, Agent, or Firm*—Schiff Hardin & Waite

(57) ABSTRACT

In a method and apparatus for catheter navigation in three-dimensional vascular tree exposures, particularly for intercranial application, the catheter position is detected and mixed into the 3D image of the pre-operatively scanned vascular tree reconstructed in a navigation computer and an imaging (registering) of the 3D patient coordination system ensues on the 3D image coordination system prior to the intervention using a number of markers placed on the patient's body, the position of these markers being registered by the catheter. The markers of a C-arm x-ray device for 3D angiography are detected in at least two 2D projection images, from which the 3D angiogram is calculated, and are projected back on to the imaged subject in the navigation computer and are brought into relation to the marker coordinates in the patient coordinate system, using projection matrices applied to the respective 2D projection images, these matrices already having been determined for the reconstruction of the 3D volume set of the vascular tree.

24 Claims, 2 Drawing Sheets

METHOD AND DEVICE FOR CATHETER NAVIGATION IN THREE-DIMENSIONAL VASCULAR TREE EXPOSURES

BACKGROUND OF THE INVENTION

1. Field of the Invention

The present invention is directed to a method and apparatus for catheter navigation in three-dimensional vascular tree exposures, in particular for intracranial application, of the type wherein the position of the catheter is detected and mixed into the 3D image of the preoperatively exposed vascular tree reconstructed in a navigation computer, and wherein imaging (registering) of 3D patient coordinate information ensues with a 3D image coordination system prior to the intervention using a number of markers placed on the patient's body, the position of these markers being registered by the catheter.

2. Description of the Prior Art

The treatment of vascular pathologies, in particular intracranial vascular pathologies, frequently ensues with the aid of a catheter that is inserted into the femoral artery and is guided through the blood vessels to the location of the treatment site. This procedure is implemented using continuously pulsed 2D-radioscopy (frequently with biplanar systems) and a contrast medium. It is often difficult for the neuro-radiologist to bring the 2D radioscopic images into coincidence with the complex three-dimensional shape of the real vascular tree. Another disadvantage of this known method is that the necessity of continuously implementing the radioscopy during the intervention entails radiation exposure for the physician and patient, and requires that the injected contrast medium be present during the entire catheter treatment, so that contrast agent must be constantly re-injected, which can have a toxic effect.

Three-dimensional images of the vascular tree can be produced by different imaging modalities, such as e.g. magnetic resonance angiography (MRA), computed tomography angiography (CTA) and 3D angiography. In 3D angiography, a 3D volume of the vascular tree is reconstructed and visualized from several, approximately 50, preoperative or intraoperative 2D x-ray projection images taken from different angles, these images generally being acquired using a C-arm x-ray device. The neuro-radiologist obtains a 3D image of the vascular tree by means of 3D exposure techniques, but has no direct knowledge about the current position of the catheter in this 3D vascular tree during the intervention. The physician must mentally image the intraoperative 2D radioscopy images, in which the catheter is depicted, onto the preoperatively scanned and reconstructed 3D vascular tree in which the catheter is not depicted, which can be laborious and time-consuming given complex vascular tree structures.

Detecting the position of the catheter using a position detection system and mixing a representation thereof into the reconstructed, three-dimensional vascular tree exposures is known, although the imaging of the 3D patient coordinate system data onto the 3D image coordinate system poses significant difficulties.

A method is disclosed in U.S. Pat. No. 5,851,183, in which the tip of a probe is detected by a position detection system and is represented in an image together with an x-ray exposure taken at the same time. In this procedure, however, only that slice is depicted from the acquired tomograms (of course, using the tip of the probe) in which the probe tip is currently located. This is, however, not comparable to the mixing a representation of a catheter tip into a three-dimensional image, to allow the catheter to be guided on the basis of this mixing so that a physician can reach the desired locations of branches of blood vessels or such. In addition, in the method according to U.S. Pat. No. 5,851,183, it is necessary to produce x-ray images with virtually no interruptions during the examination, which represents a very significant radiation exposure for the patient that one would optimally like to avoid.

SUMMARY OF THE INVENTION

An object of the present invention is to provide a method and a device of the type initially described with which the radiation exposure for the physician and patient during the intervention is reduced as is the amount of injected contrast medium during the intervention, and wherein the current catheter position is represented in a three-dimensional view of the vascular tree.

To achieve this object in a method of the type initially described, according to the present invention, given the use of a C-arm x-ray device for 3D-angiography, markers are detected in at least two 2D-projection images, from which the 3D-angiogram is calculated, and are projected back onto the imaged subject in the navigation computer and are brought into relation to the marker coordinates in the patient coordinate system using the projection matrices applied to the respective 2D-projection images, these matrices having been determined for the reconstruction of the 3D-volume set of the vascular tree, i.e. an angiographic 3D-image of the vascular tree.

The invention thereby avoids the problems hitherto existing in conventional methods of the type initially described associated with registering the catheter position in the 3D-angiography, namely when the markers still depicted in the 2D exposures do not appear as well in the 3D-image due to the size of the head and the new section that can be generated. As focal points of the respective section volume of the projection cones of the 2D-projection images used in the inventive method, the focal points of the markers can be respectively detected as 3D coordinates, most easily prior to the back-projection of a marker identified in the 2D-image, so that the focal point thereof is detected and only this point is projected back.

The inventive method enables navigating the catheter in the 3D-vascular tree during the intervention completely without intraoperative radioscopic exposures and without administering an intraoperative contrast medium.

For the registration, the marker position in the 3D image can be approached—when the markers are visible in the 3D image—for example, with the aid of a mouse, and brought into relation to the positions in the patient coordinate system, detected by touching the same markers with the catheter tip. This is possible without problem given CTA and MRA, wherein, for example, the entire head can be produced as a 3D image without problem using the markers attached to the exterior thereof. Magnetic resonance angiography (MRA) has the additional advantage that absolutely no radiation exposure occurs, not even for acquiring the pre-operative image data set for the vascular tree for the patient.

The identification of the markers can ensue interactively or even automatically, with the markers each being fashioned differently for the automatic identification, so that they can be easily and automatically differentiated by their varying form and/or size in the images. In an interactive identification, care must be taken that the markers in the patient coordinate system as well as the image coordinate system, and in turn, in each of the n projection images, are identified in the same sequence.

The visualization of the vascular tree with the mixed in catheter tip at to current position detected via the position detection system and its conversion into the image coordinate system can ensue in the 3D-surface representation, whereby the catheter tip is mixed into the three-dimensional image of the vascular tree generated by segmenting and subsequent surface rendering or volume rendering.

The 3D-visualization of the vascular tree alternately can ensue using MIP (maximum intensity projection), in which the current position of the catheter tip is imaged on the next pixel, so that the catheter tip can be mixed into the MIP display.

A "fly-through" visualization of the vascular tree from the perspective of the of the catheter tip is particularly favorable and helpful for the neuro-radiologist when navigating the catheter, this "fly-through" making a particularly simple manipulation of the catheter possible at the vascular branches.

During the intervention, it is constantly monitored whether the catheter mixed into the vascular tree is located within the imaged vessels. If this can no longer be assured during the intervention, for example, because the patient has moved somewhat despite immobilization constraints, then a registration update must be implemented. Besides a global registration update with new registration of the entire 3D vascular tree corresponding to the registration prior to the intervention, a local registration update also can be implemented with deformation of parts of the 3D vascular tree (deformable matching registration) corresponding to displacements and deformations of the vessels by the catheter. Local registration updates must be implemented on the basis of landmarks that must themselves be identified in the 3D-vascular tree, whereas the global registration updates— that are particularly helpful when changes in the patient's position occur with respect to the normally location non-variant transmitter of the position detection system, or when the currently present registration is revealed to be not sufficiently exact—can be implemented using markers placed on the head of the patient, known as "fiducial-markers".

A device for the implementation of this inventive method has a position detection system with transmitter coils arranged in the immediate proximity of the patient and a receiver built into the tip of a neuro-catheter, a navigation computer for reconstructing a 3D vascular tree from exposures of the patient acquired prior to the operation, and a registration system for imaging the patient coordinate system on the 3D image coordinate system.

The transmitter coils of the detection system are customarily arranged somewhere in the space outside of the patient's body, but it can be expedient in special cases to affix the transmitter coils directly to the patient. This has the advantage that subsequent position changes of the patient during the intervention require no registration-update since the measured position of the catheter tip does not change as a result of this position change. Another possibility to be able to detect position changes of the patient during the intervention is to firmly affix one or more receiver coils to the patient and to continuously detect their position. Thus it is possible, even after patient movement, to correctly mix the position of the receiver coil integrated into the catheter into the exposures acquired prior to or during the operation.

The markers can be variously fashioned specifically for automatic identification, and may be filled with contrast medium as warranted. The navigation computer that is provided with a visualization means for the vascular tree for mixing in the catheter tip can be a computer with a probe, or even the computer itself that is used for preparing the pre-operative 3D imaging data sets.

DESCRIPTION OF THE PREFERRED EMBODIMENTS

Figure 1:
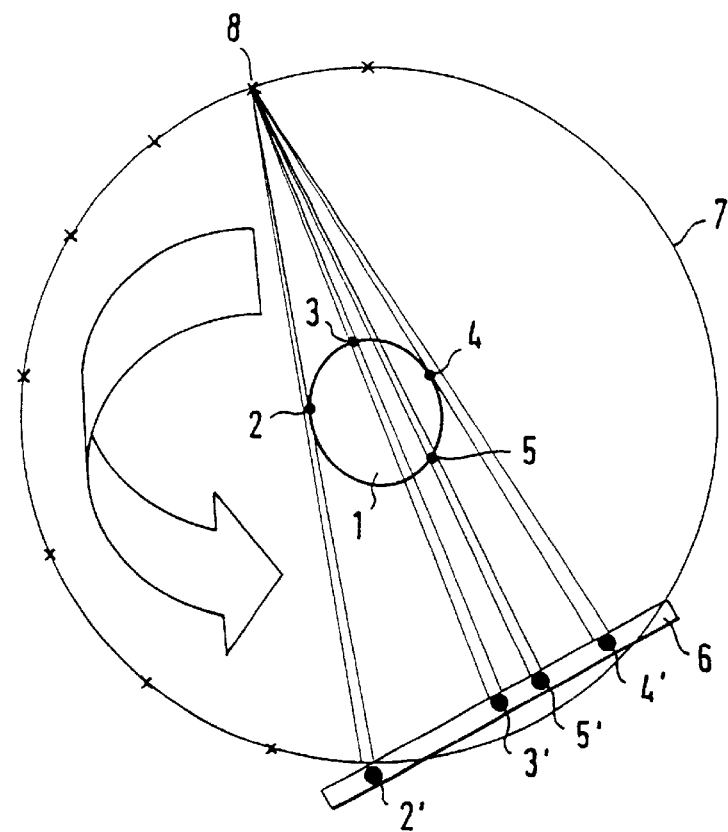
FIG. 1 is a schematic representation of a measurement subject with four markers attached and the path of the projection cone of the marker in the preparation of a 2D-projection exposure, in accordance with the inventive method and apparatus.

FIG. 1 schematically shows the head 1 of a patient, to which four markers 2 through 5 are externally affixed, that are shown in a schematically illustrated 2D-projection image 6 at respective marker image positions 2'–5'. The circle 7 shows the ideal path along which the x-ray tube and the radiation detector of a C-arm x-ray device move for 3D-angiography, with a number of further positions of the x-ray tube being indicated by crosses next to the tube focus 8 on the circle 7, from which exposures are to ensue for the 2D-projection images.

Figure 2:
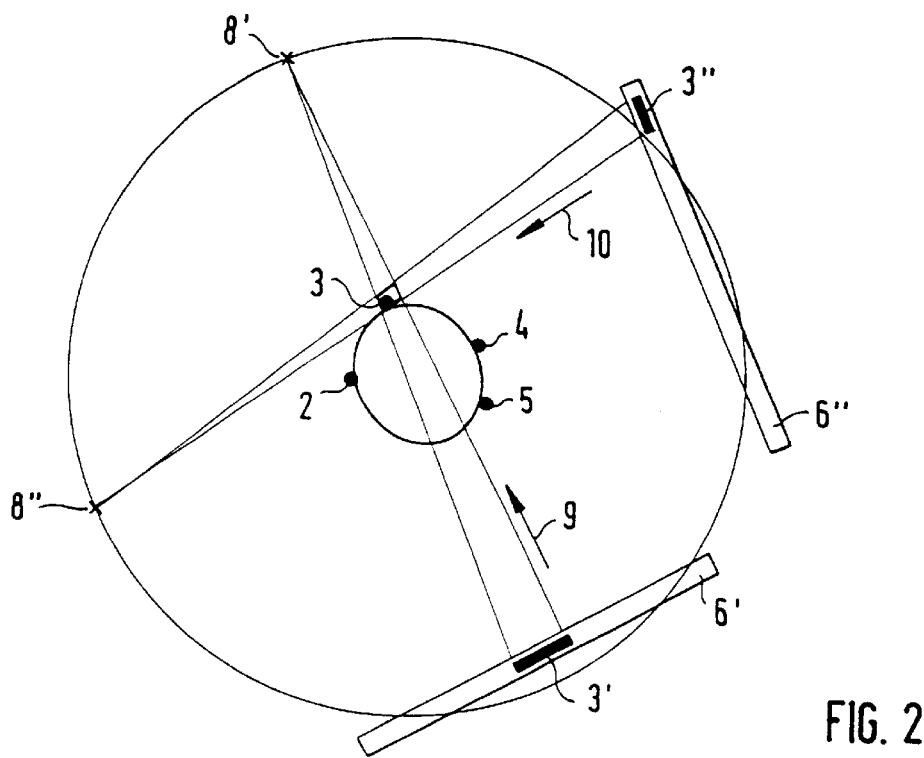
FIG. 2 illustrates the acquisition of the marker coordinates in the 3D-imaging coordinate system on the basis of the marker projections in two 2D-projection images, in accordance with the inventive method and apparatus.

FIG. 2 shows how the marker coordinates in the 3D-imaging coordinate system can be acquired at the respective tube focus positions 8' and 8" on the basis of the marker projections in two 2D-projection images 6' and 6" corresponding to the x-ray detection positions. The respective marker position images 3' and 3" of the marker 3 in the 2D-projection images 6', 6" are projected back, as is indicated by the arrows 9 and 10, with the aid of the projection image-specific projection matrices, and the intersecting volume of the two projection cones yields the position of the marker in the 3D-image.

Figure 3:
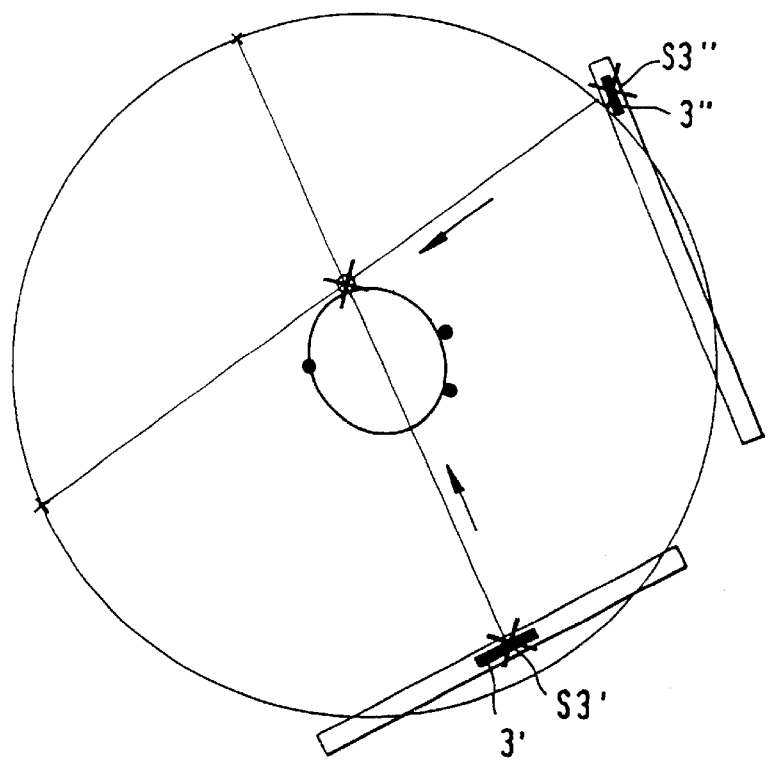
FIG. 3 is a representation corresponding to FIG. 2, in which the focal points rather than the markers themselves are projected back.

In FIG. 3, the relationships (positions) are shown in simplified form so that only the focal points S3' and S3" are projected back instead of the markers themselves.

Figure 4:
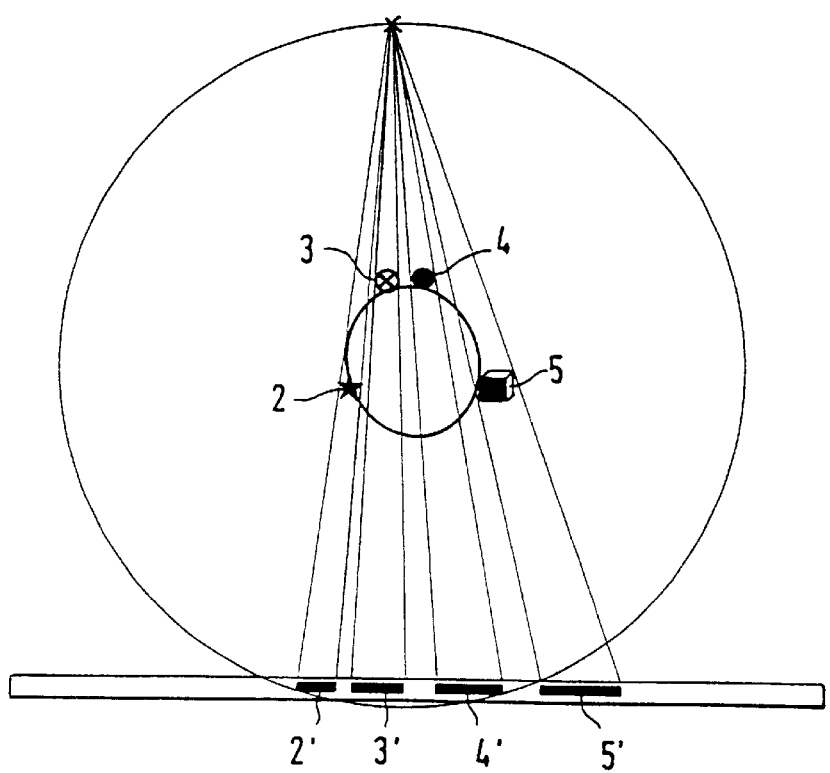
FIG. 4 is a schematic representation showing the use of variously shaped markers for the automatic identification and automatic registration in accordance with the inventive method and apparatus.

The FIG. 4 shows schematically how, using variously shaped markers 2,3,4 and 5, the prerequisite is created so that the identification and thus also the registration can ensue automatically, in that each of the markers supplies, by means of these various shapes, a unique marker position image 2'–5' that can be employed for the automatic identification.

The invention is not limited to the exemplary embodiment represented. Thus more and differently shaped markers can be used and, of course, no back-projection of the marker positions from the 2D-projection images is needed for acquiring the three-dimensional coordinates of the marker position, when the markers are visible in the 3D-image. This is, however, not the case in most instances when using 3D-angiography.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for navigating a catheter in a subject, comprising the steps of:

prior to conducting a medical intervention on a subject, attaching a plurality of markers to said subject and conducting a pre-operative 3D angiographic scan of said subject thereby obtaining a plurality of 2D projection images in which said markers are visible at respective marker positions;

from said plurality of 2D projection images, reconstructing a 3D image of a vascular tree in said subject using a plurality of projection matrices; and in said medical intervention, inserting a catheter in said subject and non-radiologically detecting a position of said catheter relative to a patient coordinate system and displaying an image of said vascular tree and said catheter in said patient coordinate system, by identifying said marker positions, as identified marker positions, in at least two of said 2D projection images and back-projecting said identified marker positions by applying respective ones of said projection matrices to said at least two of said 2D projection images to obtain back-projected coordinates of said identified marker positions in said patient coordinate system, and displaying said markers at said back-projected coordinates in said patient coordinate system in said image of said vascular tree and said catheter.

2. A method as claimed in claim 1 wherein said catheter has a catheter tip, and comprising detecting the position of said catheter using a miniaturized position detection system built into said catheter tip.

3. A method as claimed in claim 2 comprising identifying said marker positions by touching said markers corresponding to said identified marker positions with said catheter tip.

4. A method as claimed in claim 1 wherein each of said marker positions has a focal point associated therewith which defines a projection cone in said at least two of said 2D projection images, and comprising identifying said back-projected coordinates as an intersection of respective cones of said identified marker positions in said at least two of said 2D projection images.

5. A method as claimed in claim 4 comprising identifying said focal points of the respective markers in said at least 2D projection images and projecting said focal points back.

6. A method as claimed in claim 1 comprising identifying said marker positions interactively.

7. A method as claimed in claim 1 comprising identifying said marker positions automatically.

8. A method as claimed in claim 1 comprising presenting said 3D image of said vascular tree as a 3D surface representation, and mixing a position of a tip of said catheter into said 3D surface representation by segmenting and subsequent rendering selected from the group consisting of surface rendering and volume rendering.

9. A method as claimed in claim 1 comprising presenting said 3D image of said vascular tree in maximum intensity projection and wherein a current position of a tip of said catheter is depicted on a next pixel for mixing said tip of said catheter into said maximum intensity projection display.

10. A method as claimed in claim 1 comprising conducting a fly-through visualization of said vascular tree from a perspective of a tip of said catheter.

11. A method as claimed in claim 1 comprising conducting updating scanning of said examination subject during said medical intervention.

12. A method as claimed in claim 11 comprising conducting a global registration update with each new update of an entirety of said 3D vascular tree.

13. A method as claimed in claim 11 comprising a local registration update from displacement and deformation by said catheter dependent on distortion of portions of said 3D vascular tree.

14. A device for navigating a catheter in a subject, comprising:

a plurality of markers adapted to be disposed at a subject;

a 3D angiography system for, prior to conducting a medical intervention on said subject, conducting a pre-operative scan of said subject thereby obtaining a plurality of 2D projection images, in which said markers are visible at respective marker positions;

an image reconstruction computer supplied with said plurality of 2D projection images set for reconstructing a 3D image of a vascular tree in said subject from said plurality of 2D projection images using a plurality of projection matrices;

a catheter adapted for insertion in said subject in said medical intervention; and a navigation system, including a navigation computer having access to said 3D image, for non-radiologically detecting a position of said catheter relative to a patient coordinate system and for displaying said catheter in said 3D image in said patient coordinate system, said image reconstruction computer back projecting selected marker positions in at least two of said 2D projection images by applying respective ones of said projection matrices to said at least two of said 2D projection images, to obtain back-projected coordinates of said selected marker positions in said patient coordinate system, and causing said markers to be displayed at said back-projected coordinates in said patient coordinate system in said 3D image.

15. A device as claimed in claim 14 wherein said markers comprise respective transmitter coils adapted for attachment to said subject.

16. A device as claimed in claim 14 wherein said markers comprise respective receiver coils adapted for attachment to said subject.

17. A device as claimed in claim 14 wherein said markers have respectively different configurations so that each marker produces a unique representation in said 2D images.

18. A device as claimed in claim 14 wherein said navigation computer comprises a display for displaying said vascular tree as a 3D surface representation.

19. A device as claimed in claim 14 wherein said navigation computer comprises a display for representing a fly-through visualization of said vascular tree.

20. A device as claimed in claim 14 wherein said navigation computer comprises a display for maximum intensity projection display of said vascular tree.

21. A device as claimed in claim 14 wherein said 3D angiography system comprises a CT angiography system.

22. A device as claimed in claim 14 wherein said 3D angiography system comprises an MR angiography system.

23. A device as claimed in claim 14 wherein said 3D angiography system comprises a C-arm x-ray device.

24. A device as claimed in claim 23 wherein said navigation computer comprises said image reconstruction computer.

* * * * *